United States Patent
Chang et al.

(10) Patent No.: US 9,452,141 B1
(45) Date of Patent: Sep. 27, 2016

(54) ACID RESISTANT CAPSULE SHELL COMPOSITION, ACID RESISTANT CAPSULE SHELL AND ITS PREPARING PROCESS

(71) Applicant: Dah Feng Capsule Industry Co., Ltd., Taichung (TW)

(72) Inventors: Ruei-Jan Chang, Taichung (TW); Chien-Jen Wu, Taichung (TW); Yi-Huei Lin, Taichung (TW)

(73) Assignee: Dah Feng Capsule Industry Co., Ltd., Taichung (TW)

( * ) Notice: Subject to any disclaimer, the term of this patent is extended or adjusted under 35 U.S.C. 154(b) by 11 days.

(21) Appl. No.: 14/701,597

(22) Filed: May 1, 2015

(51) Int. Cl.
*A61K 9/48* (2006.01)
*A61K 47/36* (2006.01)
*A61K 47/38* (2006.01)
*A61K 31/167* (2006.01)

(52) U.S. Cl.
CPC ........... *A61K 9/4816* (2013.01); *A61K 31/167* (2013.01); *A61K 47/36* (2013.01); *A61K 47/38* (2013.01)

(58) Field of Classification Search
CPC .. A61K 9/4816; A61K 31/167; A61K 47/36; A61K 47/38
See application file for complete search history.

(56) References Cited

U.S. PATENT DOCUMENTS

| 2005/0069579 A1* | 3/2005 | Kamaguchi | A61K 9/4816 424/451 |
| 2005/0106233 A1* | 5/2005 | Andersen | A61K 9/4883 424/451 |
| 2008/0274187 A1* | 11/2008 | Cao | A61K 9/4816 424/484 |

* cited by examiner

*Primary Examiner* — Michael B Pallay
(74) *Attorney, Agent, or Firm* — Fishman & Associates, LLC.

(57) ABSTRACT

The present invention provides an acid resistant capsule shell composition comprising a water-soluble enteric polymer, a water-soluble film forming polymer, a coagulant, and a gelling aid. The water-soluble enteric polymer comprises hydrophobic functional groups and hydrophilic functional groups. The present invention further provides a process for preparing an acid resistant capsule shell comprising: dissolving said acid resistant capsule shell composition in deionized water to form a capsule shell solution; heating and then cooling the capsule shell solution to form a capsule shell stock solution; dipping a pin into the capsule shell stock solution and then removing the pin to form a film-coated pin; and drying the film-coated pin to form the acid resistant capsule shell. The acid resistant capsule shell has acidic resistance and the process for preparing the acid resistant capsule shell involves no organic solvent; hence, the problem of organic solvent residues can be prevented.

16 Claims, No Drawings

ACID RESISTANT CAPSULE SHELL COMPOSITION, ACID RESISTANT CAPSULE SHELL AND ITS PREPARING PROCESS

BACKGROUND OF THE INVENTION

1. Field of the Invention

The present invention relates to an acid resistant capsule shell composition, an acid resistant capsule shell, and a process for preparing the acid resistant capsule shell.

2. Description of the Prior Art(s)

Capsules containing drugs and shells enclosing the drugs are widely applied in oral medication field. The capsules shells prevent the drugs from direct contact with gustatory organ to cause nausea, from decomposition by saliva, and from deterioration by moisture, air, or light. The capsules shells also delay the release time of the drugs.

The main component of the commercial capsules shell is gelatin; the commercial capsules are dissolved in gastric acid and release drugs at stomach. However, release of drugs such as nonsteroidal anti-inflammatory drugs at stomach may cause serious gastric side effects such as damage of gastric mucosa, gastrorrhagia, or gastric perforation.

A conventional acid resistant capsule shell is developed to enclose the drugs, such that the drugs are released under intestinal condition instead of gastric condition to mitigate the gastric side effects of the drugs. To prepare the general acid resistant capsule, one of the conventional processes prepares a general capsule shell, loads drugs in the general capsule shell, and coats an enteric film at the outer surface of the general capsule shell. The solubility of the enteric film varies with pH value, i.e., the enteric film is soluble in alkaline condition but insoluble in acidic condition. Hence, the general acid resistant capsule can resist the gastric condition and release the drugs under intestinal condition. The component of enteric film is cellulose acetate phthalate (abbreviated as CAP), hydroxypropyl methylcellulose phthalate (abbreviated as HPMCP), hydroxypropyl methylcellulose acetate succinate (abbreviated as HPMP-AS), acrylic copolymers, or shellac. Since the components are required to be dissolved in organic solvents in the preparation, the general acid resistant capsule usually has undesired organic solvent residues, and is also complicated to be prepared.

Another conventional process for preparing a general acid resistant capsule is double dipping method, which is refined from the conventional dip molding process. A pin is dipped into a gelatin solution and an enteric coating solution subsequently, and then dried to form a general acid resistant capsule shell. Finally, drugs are loaded in the general acid resistant capsule shell to form the general acid resistant capsule. However, the component of the enteric coating solution is same with the component of the enteric film mentioned in the above paragraph; hence, the general acid resistant capsule prepared by the double dipping method also has organic solvent residues. Besides, the equipment of the double dipping method is more expensive than the equipment of the conventional dip molding process; therefore the cost of preparing the general acid resistant capsule may increase.

As stated above, there is still a need to overcome the problems such as complex process, expensive equipments, and undesired organic solvent residues.

SUMMARY OF THE INVENTION

The objective of the present invention is to modify the composition of an acid resistant capsule shell, such that the acid resistant capsule shell made from the composition can be prepared by the conventional dip molding process and equipment without organic solvent residues.

Another objective of the present invention is to render the acid resistant capsule shell an improved resistance to the gastric condition.

To achieve the foresaid objectives, the present invention provides an acid resistant capsule shell composition comprising a water-soluble enteric polymer, a water-soluble film forming polymer, a coagulant, and a gelling aid. The water-soluble enteric polymer comprises hydrophobic functional groups and hydrophilic functional groups. A molecular weight of the water-soluble enteric polymer ranges from 20 kDa to 1000 kDa, inclusive. The water-soluble film forming polymer is selected from the group consisting of gelatin, pullulan, polyvinyl alcohol, modified starch, cellulose ester, and any combination thereof. A molecular weight of the water-soluble film forming polymer ranges from 50 kDa to 815 kDa, inclusive. The coagulant comprises gellan gum or carrageen. A molecular weight of the coagulant ranges from 450 kDa to 550 kDa, inclusive. Based on the total weight of the water-soluble enteric polymer, the water-soluble film forming polymer, the coagulant, and the gelling aid, the weight percentage (wt %) of the water-soluble enteric polymer ranges from 5 wt % to 25 wt %, inclusive. The weight percentage of the water-soluble film forming polymer ranges from 71 wt % to 94.45 wt %, inclusive. The weight percentage of the coagulant ranges from 0.5 wt % to 3 wt %, inclusive. The weight percentage of the gelling aid ranges from 0.005 wt % to 1 wt %, inclusive.

The water-soluble enteric polymer has acidic resistance, i.e., the water-soluble enteric polymer is insoluble under gastric condition (pH value is about 1.2) and is soluble under intestinal condition (pH value is about 6.8). The water-soluble enteric polymer is different from the said water-soluble film forming polymer, that is, the water-soluble enteric polymer excludes gelatin, pullulan, polyvinyl alcohol, modified starch, and cellulose ester.

The acid resistant capsule shell composition can be treated as an initiator of an acid resistant capsule shell. The water-soluble enteric polymer, the water-soluble film forming polymer, the coagulant, and the gelling aid of the acid resistant capsule shell composition are all water-soluble. Hence, when the acid resistant capsule shell composition is applied to prepare the acid resistant capsule shell, the overall process for preparing the acid resistant capsule shell can be proceeded without organic solvent, and the problem of organic solvent residues can be prevented.

Preferably, the water-soluble enteric polymer comprises pectin, propylene glycol alginate (abbreviated as PGA), or xanthan gum; more preferably, the water-soluble enteric polymer comprises pectin or PGA; further preferably, the water-soluble enteric polymer comprises pectin.

Preferably, the molecular weight of the water-soluble enteric polymer ranges from 40 kDa to 400 kDa, inclusive; more preferably, the molecular weight of the water-soluble enteric polymer ranges from 50 kDa to 200 kDa, inclusive.

Preferably, a ratio of the hydrophobic functional groups to the hydrophilic functional groups of the water-soluble enteric polymer ranges from 30:70 to 70:30; more preferably, the ratio of the hydrophobic functional groups to the hydrophilic functional groups of the water-soluble enteric polymer ranges from 40:60 to 60:40; further preferably, the ratio of the hydrophobic functional groups to the hydrophilic functional groups of the water-soluble enteric polymer ranges from 45:55 to 55:45. When the ratio of the hydrophobic functional groups of the water-soluble enteric polymer is less than 30%, the acid resistant capsule shell prepared from the acid resistant capsule shell composition is more likely to be deformed due to excess absorption of water; therefore, drugs loaded in the acid resistant capsule shell are released in gastric condition.

Preferably, the hydrophobic functional groups of the water-soluble enteric polymer comprise methoxy group, propylene glycol, or their combination; the hydrophilic functional groups of the water-soluble enteric polymer comprise carboxyl group, amide group, or their combination; more preferably, the hydrophobic functional groups of the water-soluble enteric polymer comprise methoxy group; the hydrophilic functional groups of the water-soluble enteric polymer comprise carboxyl group.

Preferably, the modified starch comprises hydroxypropylated starch or hydroxyethylated starch.

Preferably, the cellulose ester comprises hydroxypropyl methylcellulose (abbreviated as HPMC), hydroxypropyl cellulose, methylcellulose, hydroxyethyl cellulose, or hydroxyethyl methylcellulose.

Preferably, a molecular weight of the water-soluble film forming polymer ranges from 50 kDa to 400 kDa, inclusive.

Preferably, the gelling aid is a salt of single-valent cation or a salt of divalent cation; more preferably, the gelling aid is a salt of single-valent cation. The salt of single-valent cation is potassium chloride (abbreviated as KCl) or sodium chloride (abbreviated as NaCl). The salt of divalent cation is calcium chloride (abbreviated as $CaCl_2$) or magnesium chloride (abbreviated as $MgCl_2$).

The present invention further provides a process for preparing an acid resistant capsule shell. The process for preparing an acid resistant capsule shell comprises: dissolving said acid resistant capsule shell composition in deionized water to form a capsule shell solution; heating and then cooling the capsule shell solution to form a capsule shell stock solution; dipping a pin into the capsule shell stock solution and then removing the pin to form a film-coated pin; and drying the film-coated pin to form the acid resistant capsule shell on the pin.

Preferably, the step of heating and then cooling the capsule shell solution to form the capsule shell stock solution comprises: heating the capsule shell solution at a temperature ranging from 65° C. to 90° C., inclusive, and then cooling the capsule shell solution to form the capsule shell stock solution. More preferably, heating the capsule shell solution is processed at the temperature ranging from 75° C. to 85° C., inclusive.

Preferably, the step of drying the film-coated pin to form the acid resistant capsule shell comprises: drying the film-coated pin at a temperature ranging from 20° C. to 90° C. to form the acid resistant capsule shell. More preferably, drying the film-coated pin is processed at the temperature ranging from 20° C. to 80° C. Further preferably, drying the film-coated pin is processed at the temperature ranging from 20° C. to 70° C.

Alternatively, drying the film-coated pin is processed at the temperature ranging from 70° C. to 80° C.

Preferably, the step of heating and then cooling the capsule shell solution to form the capsule shell stock solution comprises: heating the capsule shell solution and then cooling the capsule shell solution at a temperature ranging from 50° C. to 60° C., inclusive, to form the capsule shell stock solution.

Preferably, the temperature of the capsule shell stock solution needs to be maintained between 50° C. and 60° C., inclusive.

Preferably, the pH value of the capsule shell stock solution ranges from 4 to 6, inclusive.

The present invention further provides an acid resistant capsule shell. The acid resistant capsule shell comprises a water-soluble enteric polymer, a water-soluble film forming polymer, a coagulant, and a moisture. The water-soluble enteric polymer has hydrophobic functional groups and hydrophilic functional groups. A molecular weight of the water-soluble enteric polymer ranges from 20 kDa to 1000 kDa, inclusive. The water-soluble film forming polymer is selected from the group consisting of gelatin, pullulan, polyvinyl alcohol, modified starch, cellulose ester, and any combination thereof, and a molecular weight of the water-soluble film forming polymer ranges from 50 kDa to 815 kDa, inclusive. The coagulant comprises gellan gum or carrageen. A molecular weight of the coagulant ranges from 450 kDa to 550 kDa, inclusive. Based on the total weight of the acid resistant capsule shell, the weight percentage of the water-soluble enteric polymer ranges from 5 wt % to 25 wt %, inclusive. The weight percentage of the water-soluble film forming polymer ranges from 65 wt % to 90.5 wt %, inclusive. The weight percentage of the coagulant ranges from 0.5 wt % to 3 wt %, inclusive. The weight percentage of the moisture ranges from 4 wt % to 7 wt %, inclusive.

Preferably, the water-soluble enteric polymer comprises pectin, PGA, or xanthan gum; more preferably, the water-soluble enteric polymer comprises pectin or PGA; further preferably, the water-soluble enteric polymer comprises pectin.

Preferably, the molecular weight of the water-soluble enteric polymer ranges from 40 kDa to 400 kDa, inclusive; more preferably, the molecular weight of the water-soluble enteric polymer ranges from 50 kDa to 200 kDa, inclusive.

Preferably, a ratio of the hydrophobic functional groups to the hydrophilic functional groups of the water-soluble enteric polymer ranges from 30:70 to 70:30; more preferably, the ratio of the hydrophobic functional groups to the hydrophilic functional groups of the water-soluble enteric polymer ranges from 40:60 to 60:40; further preferably, the ratio of the hydrophobic functional groups to the hydrophilic functional groups of the water-soluble enteric polymer ranges from 45:55 to 55:45.

Preferably, the hydrophobic functional groups of the water-soluble enteric polymer comprise methoxy group, propylene glycol, or their combination; the hydrophilic functional groups of the water-soluble enteric polymer comprise carboxyl group, amide group, or their combination; more preferably, the hydrophobic functional groups of the water-soluble enteric polymer comprise methoxy group; the hydrophilic functional groups of the water-soluble enteric polymer comprise carboxyl group.

Preferably, the modified starch comprises hydroxypropylated starch or hydroxyethylated starch.

Preferably, the cellulose ester comprises HPMC, hydroxypropyl cellulose, methylcellulose, hydroxyethyl cellulose, or hydroxyethyl methylcellulose.

Preferably, a molecular weight of the water-soluble film forming polymer ranges from 50 kDa to 400 kDa, inclusive.

Other objectives, advantages and novel features of the invention will become more apparent from the following detailed description when taken in conjunction with the accompanying drawings.

DETAILED DESCRIPTION OF THE PREFERRED EMBODIMENTS

Embodiment 1

The process for preparing an acid resistant capsule shell was described as follows.

First, an acid resistant capsule shell composition was provided. The acid resistant capsule shell composition comprised a water-soluble enteric polymer, a water-soluble film forming polymer, a coagulant, and a gelling aid. The water-soluble enteric polymer has acidic resistance, i.e., the water-soluble enteric polymer is insoluble under gastric condition (about pH 1.2) and is soluble under intestinal condition (about pH 6.8). In the present embodiment, the water-soluble enteric polymer was pectin. The molecular weight of pectin ranged from 40 kDa to 400 kDa. Pectin comprised hydrophobic functional groups (methoxy group) and hydrophilic functional groups (carboxyl group). The ratio of the hydrophobic functional groups to the hydrophilic functional groups of pectin was 30:70 and the ratio of the hydrophobic functional groups to the hydrophilic functional groups of pectin was measured according to the instruction of The United States Pharmacopeial Convention <29> (abbreviated as USP<29>). The water-soluble film forming polymer was HPMC. The molecular weight of HPMC was about 80 kDa. The coagulant was gellan gum. The molecular weight of gellan gum was about 500 kDa. The gelling aid was KCl. The usages of the water-soluble enteric polymer, the water-soluble film forming polymer, the coagulant, and the gelling aid of the acid resistant capsule shell composition were listed in Table 1.

998.05 grams of the acid resistant capsule shell composition was dissolved in 6.1 kilograms of deionized water to form a capsule shell solution. The capsule shell solution was stirred at 80° C. to make the acid resistant capsule shell composition dissolve completely, and then the capsule shell solution was cooled to 55° C. to form a capsule shell stock solution. The pH value of the capsule shell stock solution was 4.5.

The capsule shell stock solution was poured into a glue pool and maintained at 50° C. to 55° C. A pin was dipped into the capsule shell stock solution and then removed to form a film-coated pin. Finally, the film-coated pin was dried at 80° C. to form a capsule shell on the pin. The acid resistant capsule shell comprised HPMC, gellan gum, pectin, and moisture. The weight percentages of said components of the acid resistant capsule shell were listed in Table 1.

TABLE 1 the usages and weight percentages of said components of the acid resistant capsule shell

| Embodiment | acid resistant capsule shell composition | | | acid resistant capsule shell | |
|---|---|---|---|---|---|
| | Component | Usage (g) | wt % | Component | wt % |
| Embodiment 1 | HPMC | 890 | 89.17 | HPMC | 84.00 |
| | Gellan gum | 8 | 0.80 | gellan gum | 0.70 |
| | Pectin | 100 | 10.02 | pectin | 9.40 |
| | KCl | 0.05 | 0.01 | moisture | 5.90 |
| | Total | 998.05 | 100.00 | Total | 100.00 |
| Embodiment 2 | pullulan | 890 | 89.17 | pullulan | 84.00 |
| | gellan gum | 8 | 0.80 | gellan gum | 0.70 |
| | pectin | 100 | 10.02 | pectin | 9.40 |
| | KCl | 0.05 | 0.01 | moisture | 5.90 |
| | Total | 998.05 | 100.00 | Total | 100.00 |
| Embodiment 3 | HPMC | 910 | 91.18 | HPMC | 86.00 |
| | gellan gum | 8 | 0.80 | gellan gum | 0.75 |
| | PGA | 80 | 8.02 | PGA | 7.50 |
| | KCl | 0.05 | 0.01 | moisture | 5.75 |
| | Total | 998.05 | 100.00% | Total | 100.00% |
| Embodiment 4 | HPMC | 840 | 84.16 | HPMC | 79.25 |
| | gellan gum | 8 | 0.80 | gellan gum | 0.75 |
| | pectin | 150 | 15.03 | pectin | 14.1 |
| | KCl | 0.05 | 0.01 | moisture | 5.9 |
| | Total | 998.05 | 100.00 | Total | 100 |
| Comparative Embodiment 1 | HPMC | 840 | 84.16 | HPMC | 84.00 |
| | gellan gum | 8 | 0.80 | gellan gum | 0.70 |
| | pectin | 150 | 15.03 | pectin | 9.40 |
| | KCl | 0.05 | 0.01 | moisture | 5.90 |
| | Total | 998.05 | 100.00 | Total | 100.00 |
| Comparative Embodiment 2 | HPMC | 890 | 89.17 | HPMC | 83.95 |
| | gellan gum | 8 | 0.80 | gellan gum | 0.75 |
| | pectin | 100 | 10.02 | pectin | 9.4 |
| | CaCl$_2$ | 0.05 | 0.01 | moisture | 5.9 |
| | Total | 998.05 | 100.00 | Total | 100 |
| Comparative Embodiment 3 | HPMC | 840 | 84.16 | HPMC | 84.00 |
| | gellan gum | 8 | 0.80 | gellan gum | 0.70 |
| | pectin | 150 | 15.03 | pectin | 9.40 |
| | KCl | 0.05 | 0.01 | moisture | 5.90 |
| | Total | 998.05 | 100.00 | Total | 100.00 |

Embodiment 2

A process for preparing an acid resistant capsule shell of the instant embodiment was similar with Embodiment 1. The difference between these two embodiments was that the water-soluble film forming polymer of Embodiment 2 was pullulan. The molecular weight of pullulan was about 805 kDa. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Embodiment 3

A process for preparing an acid resistant capsule shell of the instant embodiment was similar with Embodiment 1. The difference between these two embodiments was that the water-soluble enteric polymer was PGA. The molecular weight of PGA was about 240 kDa. PGA comprised hydrophobic functional groups (propylene glycol group) and hydrophilic functional groups (carboxyl group). The ratio of the hydrophobic functional groups to the hydrophilic functional groups of PGA was 35:65. The water-soluble film forming polymer was HPMC. The molecular weight of HPMC was about 130 kDa. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Embodiment 4

A process for preparing an acid resistant capsule shell of the instant embodiment was similar with Embodiment 1.

The difference between these two embodiments was that the ratio of the hydrophobic functional groups to the hydrophilic functional groups of pectin was 40:60. The film-coated pin was dried at 30° C. to form the acid resistant capsule shell. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Comparative Embodiment 1

This comparative embodiment provided a process for preparing an acid resistant capsule shell which was similar with Embodiment 1. The difference between Comparative Embodiment 1 and Embodiment 1 was that the ratio of the hydrophobic functional groups to the hydrophilic functional groups of pectin was 28:72. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Comparative Embodiment 2

This comparative embodiment provided a process for preparing an acid resistant capsule shell which was similar with Embodiment 1. The difference between Comparative Embodiment 2 and Embodiment 1 was that the gelling aid was calcium chloride. The capsule shell solution was stirred at 90° C. to make the acid resistant capsule shell composition dissolve completely. The film-coated pin was dried at 70° C. to form the acid resistant capsule shell. However, cracks were formed on the surface of the acid resistant capsule shell after the drying. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Comparative Embodiment 3

This comparative embodiment provided a process for preparing an acid resistant capsule shell which was similar with Embodiment 1. The difference between Comparative Embodiment 3 and Embodiment 1 was that the ratio of the hydrophobic functional groups to the hydrophilic functional groups of pectin was 72:28. The usages of the water-soluble enteric polymer, the water-soluble film forming polymer, the coagulant, and the gelling aid of the acid resistant capsule shell composition were listed in Table 1. The weight percentages of components of the acid resistant capsule shell were listed in Table 1.

Experimental Embodiment

Acetaminophen (solid powder) was loaded into the acid resistant capsule shells prepared respectively from Embodiment 1 to Embodiment 4 and Comparative Embodiment 1 to Comparative Embodiment 3 to form acid resistant capsules of said embodiments and comparative embodiments, and then the acid resistant capsules were processed with an in vitro dissolution test according to the instruction of USP<711>.

In the first stage of the in vitro dissolution test, the acid resistant capsules were put into a simulated gastric acid solution for 2 hours, and then the concentration of acetaminophen of the simulated gastric acid solution in the first stage of the in vitro dissolution test was measured. The pH value of the simulated gastric acid solution was 1.2, and the temperature of the simulated gastric acid solution was 37° C. According to the instruction of USP<711>, the dissolution rate in the first stage of the in vitro dissolution test was calculated based on the weight of acetaminophen and the concentration of acetaminophen of the simulated gastric acid solution in the first stage of the in vitro dissolution test.

The second stage of the in vitro dissolution test was processed after the first stage of the in vitro dissolution test. In the second stage of the in vitro dissolution test, the pH value of the simulated gastric acid solution was adjusted to 6.8 within 5 minutes to form a simulated intestinal solution. The acid resistant capsules were kept in the simulated intestinal solution 45 minutes, and then the concentration of acetaminophen of the simulated intestinal solution in the second stage of the in vitro dissolution test was measured. According to the instruction of USP<711>, the dissolution rate in the second stage of the in vitro dissolution test was calculated based on the weight of acetaminophen and the concentration of acetaminophen of the simulated intestinal solution in the second stage of the in vitro dissolution test. The dissolution rate in the first stage of the in vitro dissolution test and the dissolution rate in the second stage of the in vitro dissolution test of Embodiment 1 to Embodiment 4, Comparative Embodiment 1, and Comparative Embodiment 3 were listed in Table 2.

TABLE 2 the dissolution rate in the first stage of the in vitro dissolution test and the dissolution rate in the second stage of the in vitro dissolution test of Embodiment 1 to Embodiment 4, Comparative Embodiment 1, and Comparative Embodiment 3

| Embodiment | The dissolution rate in the first stage (%) | The dissolution rate in the second stage (%) |
| --- | --- | --- |
| Embodiment 1 | 9.6 | 85.7 |
| Embodiment 2 | 9.5 | 84.5 |
| Embodiment 3 | 15.4 | 60.5 |
| Embodiment 4 | 5.9 | 87.7 |
| Comparative Embodiment 1 | 35 | 50 |
| Comparative Embodiment 3 | 38 | 80 |

With reference to Table 2, the shape of the acid resistant capsule prepared from Comparative Embodiment 1 was deformed and the dissolution rate in the first stage of the in vitro dissolution test of the acid resistant capsule prepared from Comparative Embodiment 1 was 35% because the ratio of the hydrophobic functional groups to the hydrophilic functional groups of pectin was 28:72. When the ratio of the hydrophilic functional groups of pectin was too high, the acid resistant capsule was more likely to be deformed due to excess absorption of water; therefore, acetaminophen was released in gastric condition. Compared to the acid resistant capsules prepared from Embodiments 1 to 4, the dissolution rates in the first stage of the in vitro dissolution test of the acid resistant capsules prepared from Embodiments 1 to 4 were less than 16%, and the shapes of the acid resistant capsules prepared from Embodiments 1 to 4 were intact. Furthermore, the dissolution rates in the second stage of the in vitro dissolution test of the acid resistant capsules prepared from Embodiments 1 to 4 were greater than 60%, indicating that the acid resistant capsules prepared from Embodiments 1 to 4 have excellent acidic resistance.

According to the foresaid preparation of Comparative Embodiment 2, which adopted the calcium chloride as the gelling aid, the acid resistant capsule shell of Comparative Embodiment 2 was ruptured and became unusable after drying at 70° C. The acid resistant capsule of Comparative Embodiment 2 could not be examined by the first and second stages of the in vitro dissolution test. If the gelling aid is calcium chloride or other divalent cations, the film-coated pin must be dried at less than 60° C. to prevent the rupture of the acid resistant capsule shell. However, drying the film-coated pin at a low temperature prolongs the manufacturing time. Compared to the acid resistant capsule prepared from Embodiment 1, the dissolution rate in the first stage of the in vitro dissolution test of the acid resistant capsule prepared from Embodiment 1 was less than 10% and the shape of the acid resistant capsule prepared from Embodiment 1 was intact. That is to say, the film-coated pin of the acid resistant capsule shell of Embodiment 1 could be dried at a higher temperature than that of Comparative Example 2, and thus the acid resistant capsule shell of Embodiment 1 made from said composition is more beneficial for rapid production.

The dissolution rate in the first stage of the in vitro dissolution test of the acid resistant capsule prepared from Comparative Embodiment 3 was 38% because the ratio of the hydrophobic functional groups to the hydrophilic functional groups of pectin was 72:28. When the ratio of the hydrophobic functional groups of pectin was too high, the acid resistant capsule was more likely to be dissolved in simulated gastric acid solution; therefore, acetaminophen was released.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An acid resistant capsule shell composition comprising:
   a water-soluble enteric polymer having hydrophobic functional groups and hydrophilic functional groups, a molecular weight of the water-soluble enteric polymer ranging from 20 kDa to 1000 kDa;
   a water-soluble film forming polymer selected from the group consisting of gelatin, pullulan, polyvinyl alcohol, modified starch, cellulose ester, and any combination thereof, a molecular weight of the water-soluble film forming polymer ranging from 50 kDa to 815 kDa;
   a coagulant comprising gellan gum or carragean, a molecular weight of the coagulant ranging from 450 kDa to 550 kDa; and
   a gelling aid;
   wherein based on the total weight of the water-soluble enteric polymer, the water-soluble film forming polymer, the coagulant, and the gelling aid, the weight percentage of the water-soluble enteric polymer ranges from 5 wt % to 25 wt %, the weight percentage of the water-soluble film forming polymer ranges from 71 wt % to 94.45 wt %, the weight percentage of the coagulant ranges from 0.5 wt % to 3 wt %, and the weight percentage of the gelling aid ranges from 0.005 wt % to 1 wt %.

2. The acid resistant capsule shell composition as claimed in claim 1, wherein a ratio of the hydrophobic functional groups to the hydrophilic functional groups of the water-soluble enteric polymer ranges from 30:70 to 70:30.

3. The acid resistant capsule shell composition as claimed in claim 2, wherein the ratio of the hydrophobic functional groups to the hydrophilic functional groups of the water-soluble enteric polymer ranges from 40:60 to 60:40.

4. The acid resistant capsule shell composition as claimed in claim 3, wherein the ratio of the hydrophobic functional groups to the hydrophilic functional groups of the water-soluble enteric polymer ranges from 45:55 to 55:45.

5. The acid resistant capsule shell composition as claimed in claim 1, wherein the hydrophobic functional groups of the water-soluble enteric polymer comprise methoxy group, propylene glycol, or their combination; the hydrophilic functional groups of the water-soluble enteric polymer comprise carboxyl group, amide group, or their combination.

6. The acid resistant capsule shell composition as claimed in claim 5, wherein the hydrophobic functional groups of the water-soluble enteric polymer comprise methoxy group; the hydrophilic functional groups of the water-soluble enteric polymer comprise carboxyl group.

7. The acid resistant capsule shell composition as claimed in claim 1, wherein the water-soluble enteric polymer comprises pectin, propylene glycol alginate, or xanthan gum.

8. The acid resistant capsule shell composition as claimed in claim 7, wherein the water-soluble enteric polymer comprises pectin or propylene glycol alginate.

9. The acid resistant capsule shell composition as claimed in claim 8, wherein the water-soluble enteric polymer comprises pectin.

10. The acid resistant capsule shell composition as claimed in claim 1, wherein the gelling aid is a salt of single-valent cation or a salt of divalent cation.

11. The acid resistant capsule shell composition as claimed in claim 10, wherein the gelling aid is a salt of single-valent cation.

12. The acid resistant capsule shell composition as claimed in claim 1, wherein the molecular weight of the water-soluble enteric polymer ranges from 40 kDa to 400 kDa.

13. The acid resistant capsule shell composition as claimed in claim 12, wherein the molecular weight of the water-soluble enteric polymer ranges from 50 kDa to 200 kDa.

14. A process for preparing an acid resistant capsule shell comprising steps of:
   dissolving the acid resistant capsule shell composition as claimed in claim 1 in deionized water to form a capsule shell solution;
   heating and then cooling the capsule shell solution to form a capsule shell stock solution;
   dipping a pin into the capsule shell stock solution and then removing the pin to form a film-coated pin; and
   drying the film-coated pin to form the acid resistant capsule shell.

15. The process for preparing an acid resistant capsule shell as claimed in claim 14, wherein the step of heating and then cooling the capsule shell solution to form the capsule shell stock solution comprises:
   heating the capsule shell solution at a temperature ranging from 65° C. to 90° C. and then cooling the capsule shell solution to form the capsule shell stock solution.

16. The process for preparing an acid resistant capsule shell as claimed in claim 14, wherein the step of drying the film-coated pin to form the acid resistant capsule shell comprises:

drying the film-coated pin at a temperature ranging from 20° C. to 90° C. to form the acid resistant capsule shell.

\* \* \* \* \*